United States Patent
Bird et al.

(10) Patent No.: US 6,262,346 B1
(45) Date of Patent: *Jul. 17, 2001

(54) RIPENING-RELATED DNAS FROM BANANA

(75) Inventors: Colin Roger Bird, Bracknell; Jonathon David Fletcher, Maidenhead, both of (GB)

(73) Assignee: Zeneca Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/231,240

(22) Filed: Jan. 15, 1999

Related U.S. Application Data

(63) Continuation of application No. 08/632,598, filed on Apr. 15, 1996, now Pat. No. 5,886,164.

(51) Int. Cl.$^7$ .............................. A01H 5/00; A01H 5/08; C12N 15/82
(52) U.S. Cl. ........................... 800/298; 800/283; 800/286
(58) Field of Search ................................ 435/69.1, 320.1, 435/419, 468; 536/23.2, 23.6; 800/278, 286, 283, 298

(56) References Cited

U.S. PATENT DOCUMENTS

| | | | |
|---|---|---|---|
| 5,723,766 | * | 3/1998 | Theologis et al. ................. 800/205 |
| 5,886,164 | * | 3/1999 | Bird et al. ......................... 536/23.2 |

FOREIGN PATENT DOCUMENTS

91/08299   6/1991   (WO).

OTHER PUBLICATIONS

Smith, C.J.S., et al., Nature, "Antisense RNA inhibition of polygalacturonase gene expression in transgenic tomatoes", vol. 334, 1988, pp. 724–726.

Bevan, M., Nucleic Acids Research, "Binary Agrobacterium vectors for plant transformation", vol. 12, No. 22, 1984, pp. 8711–8721.

Bird, C.R., et al., Biotechnology and Genetic Engineering Reviews, "Manipulation of Plant Gene Expression by Antisense RNA", vol. 9, 1991, pp. 207–227.

Gray, J., et al., Plant Molecular Biology, "Molecular biology of fruit ripening and its manipulation with antisense genes", vol. 19, 1992, pp. 69–87.

May, G.D., et al., Biotechnology, "Generation of Transgenic Banana (*Musa acuminata*) Plants via Agrobacterium–Mediated Transformation", vol. 13, 1995, pp. 486–492.

Hamilton, A.J., et al., Nature, "Antisense gene that inhibits synthesis of the hormone ethylene in transgenic plants", vol. 346, 1990, pp. 284–287.

Oeller, P.W., et al., Science, Reversible inhibition of tomato fruit senescence by antisense RNA, vol. 254, 1991, pp. 437–439.

Koziel, M.G., et al. Plant Mol. Biol. "Optimizing expression of transgenes with an emphasis of post–transcriptional events", vol. 32, 1996, pp. 393–405.

Stam, M. et al., Ann. Bot., "The silence of genes in transgenic plants", vol. 79, 1997, pp. 3–12.

Picton S, et al. "Altered fruit ripening and leaf senescence in tomatoes expressing an antisense ethylene–forming enzyme transgene." Plant J. 3: 469–481, 1993.*

May GD, et al. "Generation of transgenic banana (*Musa acuminata*) plants via Agrobacterium–mediated transformation." Bio/Technology 13: 486–492, May 1995.*

* cited by examiner

Primary Examiner—Amy J. Nelson
(74) Attorney, Agent, or Firm—Liza D. Hohenschutz

(57) ABSTRACT

A method of modifying ethylene biosynthesis in a plant comprises inserting into the genome of the said plant a DNA sequence such as SEQ-ID-NO-1 (encoding 1-aminocyclopropane-1-carboxylic acid synthase (ACS)) and/or sequence SEQ-ID-NO-2 (encoding an ethylene-forming enzyme (EFE)) which modifies the activity of at least one of ACS or EFE. The method may be used to modify fruit ripening characteristics, especially in bananas.

6 Claims, No Drawings

SEQUENCE LISTING (1) GENERAL INFORMATION:

(iii) NUMBER OF SEQUENCES: 50

(2) INFORMATION FOR SEQ ID NO:1:

(i) SEQUENCE CHARACTERISTICS:
        (A) LENGTH: 1712 base pairs
        (B) TYPE: nucleic acid
        (C) STRANDEDNESS: single
        (D) TOPOLOGY: linear (ii) MOLECULE TYPE: cDNA (vi) ORIGINAL SOURCE:

(A) ORGANISM: MUSA (vii) IMMEDIATE SOURCE:
(B) CLONE: ACS GENE (xi) SEQUENCE DESCRIPTION: SEQ ID NO:1:

| | | | | | |
|---|---|---|---|---|---|
| AAAACCTACA | CACCGGGTCA | CATGAGGATC | TACGGCGAGG | AGCACCCAAA | TCAGCAGATC | 60 |
| CTCTCTCGGA | TCGCGACCAA | CGACGGCCAT | GGCGAGAACT | CCTCCTACTT | CGATGGCTGG | 120 |
| AAGGCCTACG | AGAAGGATCC | TTTCCACCTC | ACCGACAACC | CCACGGGGGT | CATCCAAATG | 180 |
| GGACTCGCAG | AAAACCAGCT | TTCCCTCGAC | TTGATCCGAG | ACTGGATGAA | GAAGAACCCA | 240 |
| CAGGCTTCGA | TCTGCACCGA | AGAAGGGGTC | TCAGAGTTCA | AAGCAATTGC | CAACTTTCAG | 300 |
| GACTATCATG | GCCTCCCAAC | CTTCCGAAAG | GCCATCGCCC | AGTTCATGGA | GAAGGTGAGA | 360 |
| GGGGGACGAG | CCAGATTTGA | CCCAGACCGC | ATCGTGATGA | GCGGTGGAGC | CACCGGCGCT | 420 |
| CAGGAAACCA | TCGCCTTTTG | CCTGGCTGAT | CCTGGCGAGG | CCTTCTTGAT | TCCAACGCCA | 480 |
| TATTATCCGG | GATTCGATCG | AGACTTCAGG | TGGAGGACAG | GAGTTCAGCT | CCTCCCCATT | 540 |
| CACTGCCACA | GTTCCAACAA | GTTCAAGATC | ACCCTTGCCG | CACTGGAGAC | TGCTTACAGG | 600 |
| AAGGCTCGAA | ACTCACACAT | TAGAGTCAAA | GGAATACTGG | TGACCAACCC | ATCGAACCCT | 660 |
| CTGGGCACAA | CCATGGACAG | AGAGACGCTG | AGAACCCTAG | TCAGCTTCGT | CAACGAGAAA | 720 |
| AGGATGCACT | TGGTGTGCGA | CGAGATCTTC | TCCGGAACCG | TCTTCGACAA | GCCGAGTTAC | 780 |
| GTGAGCGTCT | CCGAGGTGAT | CGAAGACGAG | CCCTACTGCG | ACAGGGATCT | GATTCACATC | 840 |
| GCCTACAGCC | TCTCCAAGGA | CCTGGGCGTC | CCTGGCTTCC | GCGTCGGCGT | CATATACTCC | 900 |
| TACAACGACG | CCGTGGTCAG | CTGCGCGAGG | AAGATGTCGA | GCTTTGGACT | GGTCTCGTCG | 960 |
| CAGACGCAGC | TCCTGCTCGC | TTCCATGTTG | GGAGACGAGG | AGTTCACCAC | GAGTTTCTTA | 1020 |
| GCGACGAGCC | GGACGAGGTT | GTGCGGGCGG | CGCAGGGTCT | TTACGACGG | CCTCAAGCGA | 1080 |
| GTCGGGATTC | ATTGCTTGGA | CGGCAACGCG | GGGCTGTTCT | GCTGGATGGA | CTTGAGGCCG | 1140 |
| TTGCTGAAGG | AAGCGACGGT | GGAGGCGGAC | GTCCGGCTGT | GGCGGGTGAT | CATCAACGAC | 1200 |
| GTGAAGCTCA | ACATCTCGCC | GGGGTCGTCC | TTCCACTGCT | CGGAGCCGGG | GTGGTTCAGG | 1260 |
| GTGTGCTTCG | CCAACATGGA | CGACACGGCC | ATGAAGATAG | CGCTGAGGAG | GATCGAGAGT | 1320 |
| TTCGTGTACC | GGGAGAACGA | CGCCGCTGTG | CAGGCGAAGA | ACAAGAGGAG | GTGGGACGAA | 1380 |
| GCGCTGCGGC | TGAGCTTGCC | TCGTCGGAGG | TTCGAGGATC | CGTCCATCAT | GACACCACAT | 1440 |
| CTGATGTCTC | CCCACTCGCC | TCTCGTTCAA | GCCGCCACCT | GAAACATCGA | CAGCGGCGTG | 1500 |
| TCTGATGTCA | AAGAAGGTTA | ATTACCGTCT | GATATGTTGC | ACATTTCTTT | GTTCTTTGGA | 1560 |
| TTATTTATTT | TTTTTTTTGG | GAAAAATGGG | TTGAATGTTC | CCACTAAGTT | ATATTAGATT | 1620 |
| GTTATTCGGT | CTCATTCATG | TTATAGGAAA | CGAGGATAGA | ATTGCTTGCC | TCTCTCTTTC | 1680 |
| TTTTATATAT | GGAAATATGT | TGCAATTGGC | CT | | | 1712 |

(2) INFORMATION FOR SEQ ID NO:2:

(i) SEQUENCE CHARACTERISTICS:
(A) LENGTH: 1181 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: MUSA (vii) IMMEDIATE SOURCE:
    (B) CLONE: EFE GENE (xi) SEQUENCE DESCRIPTION: SEQ ID NO:2:

| | | | | | |
|---|---|---|---|---|---|
| AAAACCACAC | ACCACAAGTG | CAATCAGGGA | AGAAAGAGCG | TGTCATGGAT | TCCTTTCCGG | 60 |
| TTATCGACAT | GGAGAAGCTT | TTGGGAAGGG | AGAGAGGAGC | AGCCATGGAG | ATCCTCCGAG | 120 |
| ATGCTTGCGA | GAAATGGGGC | TTCTTTGAGA | TTTTAAACCA | TGGCATCTCA | CATGACCTCA | 180 |
| TGGATGAAGT | GGAGAAGGTG | AACAAAGAAC | AGTACAACAA | ATGCAGGGAG | CAAAAGTTCA | 240 |
| ACGAGTTCGC | CAACAAAGCA | CTGGAAAACG | CCGACTCAGA | AATCGACCAC | CTCGACTGGG | 300 |
| AAAGCACCTT | TTTCCTGCGT | CATCTCCCCG | TCTCCAACAT | TTCTGAGATC | CCCGATCTTG | 360 |
| ATGACCAGTA | TAGGAAGGCG | ATGAAGGAAT | TTGCTGCAGC | GATAGAGAAG | CTGGCAGAGC | 420 |
| GGCTGCTCGA | CTTGCTGGGT | GAGAACCTGG | AGCTGGAGAA | GGGGTACCTG | AAGAAAGCCT | 480 |
| TCTCTAATGG | ATCCAAGGGG | CCAACCTTTG | GACCAAGGT  | CAGCAGCTAC | CCACCATGCC | 540 |
| CACGCCCGGA | CCTGGTGAAG | GGCCTGAGGG | CGCACACCGA | CGCCGGAGGC | ATCATCTTGC | 600 |
| TCTTCCAGGA | CGACCAGGTC | AGCGGCCTGC | AGTTCCTCAA | GGACGGCGAG | TGGCTGGACG | 660 |
| TGCCCCCCAT | GCGCCATGCC | ATCGTCGTCA | ACCTCGGCGA | CCAGCTCGAG | GTAATCACCA | 720 |
| ATGGCAAGTA | CAAGAGCGTG | GTGCACCGCG | TGGTGGCTCA | GACTGATGGC | AACAGGATGT | 780 |
| CGATTGCCTC | CTTCTACAAC | CCCGGGAGCG | ACGCTGTGAT | CTTCCCGGCC | CCGCTCTTG  | 840 |
| TGGAGAAGGA | AGCGGAGGAG | AAGAAGGAGG | TCTATCCGAG | GTTCGTGTTC | GAGGATTACA | 900 |
| TGAAGCTCTA | CGTCGGGCAT | AAGTTCCAGG | CCAAGGAGCC | AAGATTCGAA | GCCATGAAAG | 960 |
| CCATGGAAGC | AGTTGCCACC | CACCCAATCG | CTACCTCTTA | AGTGACAGCC | CCCAAGTTAG | 1020 |
| TGCATGTCGC | TGTACTTCGC | GTTAGGAAGC | TGTCGTCTAT | GTCTATGTAA | CCCGATGGAA | 1080 |
| GCGTGGTATG | TACGTGTTTG | AGCCTTTTCT | AATGAAGCAA | GTCATATAAT | ATATATATAT | 1140 |
| ATATATATAT | ATATATATAT | ATATATAAAT | AATTACTCTT | C | | 1181 |

(2) INFORMATION FOR SEQ ID NO:3:

(i) SEQUENCE CHARACTERISTICS:
        (A) LENGTH: 7 amino acids
        (B) TYPE: amino acid
        (D) TOPOLOGY: unknown (ii) MOLECULE TYPE: peptide (vi) ORIGINAL SOURCE:
        (A) ORGANISM: LYCOPERSICON ESCULENTUM (vii) IMMEDIATE SOURCE:
        (B) CLONE: 5' PRIMER (xi) SEQUENCE DESCRIPTION: SEQ ID NO:3:

Phe Gln Asp Tyr His Gly Leu
1               5

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: LYCOPERSICON ESCULENTUM (vii) IMMEDIATE SOURCE:
              (B) CLONE: OLIGONUCLEOTIDE PROBE 5' PRIMER (xi) SEQUENCE DESCRIPTION: SEQ ID NO:4:

TTTCAAGATT ATCATGGCTT G                                              21

(2) INFORMATION FOR SEQ ID NO:5:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: cDNA (vi) ORIGINAL SOURCE:
              (A) ORGANISM: SQUASH (vii) IMMEDIATE SOURCE:
              (B) CLONE: OLIGONUCLEOTIDE PROBE 5' PRIMER (xi) SEQUENCE DESCRIPTION: SEQ ID NO:5:

TTTCAAGATT ACCATGGCTT A                                              21

(2) INFORMATION FOR SEQ ID NO:6:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: cDNA (vi) ORIGINAL SOURCE:
              (A) ORGANISM: MUNG BEAN (vii) IMMEDIATE SOURCE:
              (B) CLONE: OLIGONUCLEOTIDE PROBE 5' PRIMER (xi) SEQUENCE DESCRIPTION: SEQ ID NO:6:

TTTCAGGATT ACCATGGTCT G                                              21

(2) INFORMATION FOR SEQ ID NO:7:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: cDNA (vi) ORIGINAL SOURCE:
              (A) ORGANISM: TOBACCO (vii) IMMEDIATE SOURCE:
              (B) CLONE: OLIGONUCLEOTIDE PROBE 5' PRIMER (xi) SEQUENCE DESCRIPTION: SEQ ID NO:7:

TTTCAAGATT ATCACGGCCT A                                              21

(2) INFORMATION FOR SEQ ID NO:8:

(i) SEQUENCE CHARACTERISTICS:
              (A) LENGTH: 21 base pairs
              (B) TYPE: nucleic acid
              (C) STRANDEDNESS: single
              (D) TOPOLOGY: linear

```
        (ii) MOLECULE TYPE: cDNA (vi) ORIGINAL SOURCE:
              (A) ORGANISM: CARNATION (vii) IMMEDIATE SOURCE:
              (B) CLONE: OLIGONUCLEOTIDE PROBE (xi) SEQUENCE DESCRIPTION: SEQ ID NO:8:

TTTCAGGATT ATCATGGTTT G                                              21

(2) INFORMATION FOR SEQ ID NO:9:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: cDNA (vi) ORIGINAL SOURCE:
              (A) ORGANISM: MOTH ORCHID (vii) IMMEDIATE SOURCE:
              (B) CLONE: OLIGONUCLEOTIDE PROBE 5' PRIMER (xi) SEQUENCE DESCRIPTION: SEQ ID NO:9:

TTTCAGGACT ATCATGGCCT C                                              21

(2) INFORMATION FOR SEQ ID NO:10:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: cDNA (vii) IMMEDIATE SOURCE:
              (B) CLONE: DEGENERATE OLIGONUCLEOTIDE PROBE (xi) SEQUENCE DESCRIPTION: SEQ ID NO:10:

TTTCARGAYT AYCAYGGYYT G                                              21

(2) INFORMATION FOR SEQ ID NO:11:

(i) SEQUENCE CHARACTERISTICS:
              (A) LENGTH: 7 amino acids
              (B) TYPE: amino acid
              (D) TOPOLOGY: unknown (ii) MOLECULE TYPE: peptide (vi) ORIGINAL SOURCE:
              (A) ORGANISM: LYCOPERSICON ESCULENTUM (vii) IMMEDIATE SOURCE:
              (B) CLONE: PROBE  3' PRIMER (xi) SEQUENCE DESCRIPTION: SEQ ID NO:11:

Pro Ser Asn Pro Leu Gly Thr
1               5

(2) INFORMATION FOR SEQ ID NO:12:

(i) SEQUENCE CHARACTERISTICS:
              (A) LENGTH: 21 base pairs
              (B) TYPE: nucleic acid
```

```
            (C) STRANDEDNESS: single
            (D) TOPOLOGY: linear (ii) MOLECULE TYPE: cDNA (vi) ORIGINAL SOURCE:
            (A) ORGANISM: LYCOPERSICON ESCULENTUM (vii) IMMEDIATE SOURCE:
            (B) CLONE: OLIGONUCLEOTIDE PROBE 3' PRIMER (xi) SEQUENCE DESCRIPTION: SEQ ID NO:12:

CCATCAAATC CATTGGGCAC C                                            21

(2) INFORMATION FOR SEQ ID NO:13:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: SQUASH (vii) IMMEDIATE SOURCE:
            (B) CLONE: OLIGONUCLEOTIDE PROBE 3' PRIMER (xi) SEQUENCE DESCRIPTION: SEQ ID NO:13:

CCCTCAAATC CCTTAGGCAC A                                            21

(2) INFORMATION FOR SEQ ID NO:14:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: MUNG BEAN (vii) IMMEDIATE SOURCE:
            (B) CLONE: OLGIONUCLEOTIDE PROBE 3' PRIMER (xi) SEQUENCE DESCRIPTION: SEQ ID NO:14:

CCATCAAATC CATTAGGCAC A                                            21

(2) INFORMATION FOR SEQ ID NO:15:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: TOBACCO (vii) IMMEDIATE SOURCE:
            (B) CLONE: OLIGONUCLEOTIDE PROBE 3' PRIMER (xi) SEQUENCE DESCRIPTION: SEQ ID NO:15:

CCATCAAATC CATTAGGCAC C                                            21
```

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: MOTH ORCHID (vii) IMMEDIATE SOURCE:
        (B) CLONE: OLIGONUCLEOTIDE PROBE 3' PRIMER (xi) SEQUENCE DESCRIPTION: SEQ ID NO:16:

```
CCTTCGAATC CTCTGGGCAC C                                              21
```

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: DEGENERATE OLIGONUCLEOTIDE PROBE (xi) SEQUENCE DESCRIPTION: SEQ ID NO:17:

```
BGTKCCYARD GGATTTSABG G                                              21
```

(2) INFORMATION FOR SEQ ID NO:18:

(i) SEQUENCE CHARACTERISTICS:
        (A) LENGTH: 211 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: BANANA (vii) IMMEDIATE SOURCE:
        (B) CLONE: pBASH14

(xi) SEQUENCE DESCRIPTION: SEQ ID NO:18:

```
TTTCAGGACT ACCATGGTCT GCCGGACTTC CGTAAGTAAT CACCGTCTGC ATCCATAATG     60

CAGCTCCTCG ATCCTTACGC ATGCGTGCCA TGAACGATGA GGGCACAGTT GGATCGATAT    120

GCGTTGCTAT AGCCGAAAGT AATGACGCGA TCATCTATGG AAATGCACAG GCCATTGCCA    180

AGTTCATGGA GAAAGCGAGA GGAGGACGAG C                                   211
```

(2) INFORMATION FOR SEQ ID NO:19:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: BANANA

```
        (vii) IMMEDIATE SOURCE:
              (B) CLONE: TRANSLATION OF pBASH14

(xi) SEQUENCE DESCRIPTION: SEQ ID NO:19:

Phe Gln Asp Tyr His Gly Leu Pro Asp Phe Arg Lys
1               5                   10

(2) INFORMATION FOR SEQ ID NO:20:

(i) SEQUENCE CHARACTERISTICS:
              (A) LENGTH: 12 amino acids
              (B) TYPE: amino acid
              (C) STRANDEDNESS: single
              (D) TOPOLOGY: unknown (ii) MOLECULE TYPE: peptide (vi) ORIGINAL SOURCE:
              (A) ORGANISM: LYCOPERSICON ESCULENTUM (vii) IMMEDIATE SOURCE:
              (B) CLONE: TOMACC1

(xi) SEQUENCE DESCRIPTION: SEQ ID NO:20:

Phe Gln Asp Tyr His Gly Leu Pro Glu Phe Arg Lys
1               5                   10

(2) INFORMATION FOR SEQ ID NO:21:

(i) SEQUENCE CHARACTERISTICS:
              (A) LENGTH: 12 amino acids
              (B) TYPE: amino acid
              (C) STRANDEDNESS: single
              (D) TOPOLOGY: unknown (ii) MOLECULE TYPE: peptide (vi) ORIGINAL SOURCE:
              (A) ORGANISM: LYCOPERSICON ESCULENTUM (vii) IMMEDIATE SOURCE:
              (B) CLONE: TOMACC2

(xi) SEQUENCE DESCRIPTION: SEQ ID NO:21:

Phe Gln Asp Tyr His Gly Leu Pro Glu Phe Thr Asn
1               5                   10

(2) INFORMATION FOR SEQ ID NO:22:

(i) SEQUENCE CHARACTERISTICS:
              (A) LENGTH: 13 amino acids
              (B) TYPE: amino acid
              (C) STRANDEDNESS: single
              (D) TOPOLOGY: unknown (ii) MOLECULE TYPE: peptide (vi) ORIGINAL SOURCE:
              (A) ORGANISM: BANANA (vii) IMMEDIATE SOURCE:
              (B) CLONE: TRANSLATION OF pBASH14

(xi) SEQUENCE DESCRIPTION: SEQ ID NO:22:

Ala Ile Ala Lys Phe Met Glu Lys Ala Arg Gly Gly Arg
1               5                   10

(2) INFORMATION FOR SEQ ID NO:23:

(i) SEQUENCE CHARACTERISTICS:
              (A) LENGTH: 13 amino acids
```

```
        (B) TYPE: amino acid
        (C) STRANDEDNESS: single
        (D) TOPOLOGY: unknown (ii) MOLECULE TYPE: peptide (vi) ORIGINAL SOURCE:
        (A) ORGANISM: LYCOPERSICON ESCULENTUM (vii) IMMEDIATE SOURCE:
        (B) CLONE: TOMACC1

(xi) SEQUENCE DESCRIPTION: SEQ ID NO:23:

Ala Ile Ala Lys Phe Met Glu Lys Thr Arg Gly Gly Arg
1               5                   10

(2) INFORMATION FOR SEQ ID NO:24:

(i) SEQUENCE CHARACTERISTICS:
        (A) LENGTH: 13 amino acids
        (B) TYPE: amino acid
        (C) STRANDEDNESS: single
        (D) TOPOLOGY: unknown (ii) MOLECULE TYPE: peptide (vi) ORIGINAL SOURCE:
        (A) ORGANISM: LYCOPERSICON ESCULENTUM (vii) IMMEDIATE SOURCE:
        (B) CLONE: TOMACC2

(xi) SEQUENCE DESCRIPTION: SEQ ID NO:24:

Ala Ile Ala Lys Phe Met Glu Lys Thr Arg Gly Gly Lys
1               5                   10

(2) INFORMATION FOR SEQ ID NO:25:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: peptide (vii) IMMEDIATE SOURCE:
        (B) CLONE: 5' PRIMER (xi) SEQUENCE DESCRIPTION: SEQ ID NO:25:

Asp Trp Glu Ser Thr Phe Phe
1               5

(2) INFORMATION FOR SEQ ID NO:26:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: LYCOPERSICON ESCULTENTUM (vii) IMMEDIATE SOURCE:
        (B) CLONE: 5' PRIMER (xi) SEQUENCE DESCRIPTION: SEQ ID NO:26:

GATTGGGAAA GCACTTTCTT C                                                   21
```

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: MELON (vii) IMMEDIATE SOURCE:
        (B) CLONE: 5' PRIMER (xi) SEQUENCE DESCRIPTION: SEQ ID NO:27:

GACTGGGAAA GCACTTTTTT T                                               21

(2) INFORMATION FOR SEQ ID NO:28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: PEACH (vii) IMMEDIATE SOURCE:
        (B) CLONE: 3' PRIMER (xi) SEQUENCE DESCRIPTION: SEQ ID NO:28:

GACTGGGAAA GCACCTTCTA C                                               21

(2) INFORMATION FOR SEQ ID NO:29:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: AVOCADO (vii) IMMEDIATE SOURCE:
        (B) CLONE: 5' PRIMER (xi) SEQUENCE DESCRIPTION: SEQ ID NO:29:

GACTGGGAGA GCACCTTCTT C                                               21

(2) INFORMATION FOR SEQ ID NO:30:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: MUSTARD (vii) IMMEDIATE SOURCE:
        (B) CLONE: 5' PRIMER (xi) SEQUENCE DESCRIPTION: SEQ ID NO:30:

GATTGGGAAA GCACTTTCTA C                                              21

(2) INFORMATION FOR SEQ ID NO:31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: APPLE (vii) IMMEDIATE SOURCE:
        (B) CLONE: 5' PRIMER (xi) SEQUENCE DESCRIPTION: SEQ ID NO:31:

GACTGGGAAA GCACCTTCTT C                                              21

(2) INFORMATION FOR SEQ ID NO:32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: CARNATION (vii) IMMEDIATE SOURCE:
        (B) CLONE: 5' PRIMER (xi) SEQUENCE DESCRIPTION: SEQ ID NO:32:

GATTGGGAGA GCACCTTCTA C                                              21

(2) INFORMATION FOR SEQ ID NO:33:

(i) SEQUENCE CHARACTERISTICS:
        (A) LENGTH: 19 base pairs
        (B) TYPE: nucleic acid
        (C) STRANDEDNESS: single
        (D) TOPOLOGY: unknown (ii) MOLECULE TYPE: peptide (vii) IMMEDIATE SOURCE:
        (B) CLONE: DEGENERATE OLIGONUCLEOTIDE PROBE 5'

(xi) SEQUENCE DESCRIPTION: SEQ ID NO:33:

GAYTGGGARA GCACYTTYT                                                 19

(2) INFORMATION FOR SEQ ID NO:34:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: peptide (vi) ORIGINAL SOURCE:
        (A) ORGANISM: LYCOPERSICON ESCULENTUM (vii) IMMEDIATE SOURCE:
            (B) CLONE: 3' PRIMER (xi) SEQUENCE DESCRIPTION: SEQ ID NO:34:

Val Ser Asn Tyr Pro Pro Cys
1               5

(2) INFORMATION FOR SEQ ID NO:35:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: LYCOPERSICON ESCULENTUM (vii) IMMEDIATE SOURCE:
        (B) CLONE: 3' PRIMER (xi) SEQUENCE DESCRIPTION: SEQ ID NO:35:

GTTAGCAACT ATCCACCATG T                                          21

(2) INFORMATION FOR SEQ ID NO:36:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: PEACH (vii) IMMEDIATE SOURCE:
        (B) CLONE: 3' PRIMER (xi) SEQUENCE DESCRIPTION: SEQ ID NO:36:

GTTAGCAACT ACCCTCCTTG T                                          21

(2) INFORMATION FOR SEQ ID NO:37:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: APPLE (vii) IMMEDIATE SOURCE:
        (B) CLONE: 3' PRIMER (xi) SEQUENCE DESCRIPTION: SEQ ID NO:37:

GTCAGCAACT ACCCTCCATG C                                          21

(2) INFORMATION FOR SEQ ID NO:38:

(i) SEQUENCE CHARACTERISTICS:
        (A) LENGTH: 21 base pairs
        (B) TYPE: nucleic acid
        (C) STRANDEDNESS: single
        (D) TOPOLOGY: linear

```
        (ii) MOLECULE TYPE: cDNA (vi) ORIGINAL SOURCE:
             (A) ORGANISM: AVOCADO (vii) IMMEDIATE SOURCE:
             (B) CLONE: 3' PRIMER (xi) SEQUENCE DESCRIPTION: SEQ ID NO:38:

GTCAGCAACT ACCCACCCTG C                                              21

(2) INFORMATION FOR SEQ ID NO:39:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: cDNA (vi) ORIGINAL SOURCE:
             (A) ORGANISM: MELON (vii) IMMEDIATE SOURCE:
             (B) CLONE: 3' PRIMER (xi) SEQUENCE DESCRIPTION: SEQ ID NO:39:

GTTAGCAATT ACCCCCCATG T                                              21

(2) INFORMATION FOR SEQ ID NO:40:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: cDNA (vi) ORIGINAL SOURCE:
             (A) ORGANISM: MUSTARD (vii) IMMEDIATE SOURCE:
             (B) CLONE: 3' PRIMER (xi) SEQUENCE DESCRIPTION: SEQ ID NO:40:

GTGAGCAACT ATCCAGCTTG T                                              21

(2) INFORMATION FOR SEQ ID NO:41:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: cDNA (vii) IMMEDIATE SOURCE:
             (B) CLONE: DEGENERATE OLIGONUCLEOTIDE PROBE 3'

(xi) SEQUENCE DESCRIPTION: SEQ ID NO:41:

RCADGGWGGR TARTTGCTVA C                                              21

(2) INFORMATION FOR SEQ ID NO:42:

(i) SEQUENCE CHARACTERISTICS:
             (A) LENGTH: 331 base pairs
             (B) TYPE: nucleic acid
```

(C) STRANDEDNESS: single
            (D) TOPOLOGY: linear (ii) MOLECULE TYPE: cDNA (vi) ORIGINAL SOURCE:
            (A) ORGANISM: BANANA (vii) IMMEDIATE SOURCE:
            (B) CLONE: pBEAR13

(xi) SEQUENCE DESCRIPTION: SEQ ID NO:42:

GGGAGAGCAC CTTTTTCCTG CGTCATCTCC CCGTCTCCAA CATTTCTGAG ATCCCCGATC       60

TTGATGACCA GTATAGGTTG CACGATCTGA TCATGATGTC ATCTTCTAGC CTTGTCTTTT      120

CACCTTGCTC ATCGTTTCGT TTCTTGGGAC GATGACTGCG TGCAGGAAGG CGATGAAGGA      180

ATTTGCTGCA GCGATAGAGA AGCTGGCAGA GCGGCTGCTC GACTTGCTGG GTGAGAACCT      240

GGAGCTGGAG AAGGGGCTCC TGAAGAAGGC CTTCTCTAAT GGATCCAAGG GGCCAACCTT      300

TGGGACCAAG GTCAGCAACT ACCCACCTTG C                                    331

(2) INFORMATION FOR SEQ ID NO:43:

(i) SEQUENCE CHARACTERISTICS:
            (A) LENGTH: 25 amino acids
            (B) TYPE: amino acid
            (C) STRANDEDNESS: single
            (D) TOPOLOGY: unknown (ii) MOLECULE TYPE: peptide (vi) ORIGINAL SOURCE:
            (A) ORGANISM: BANANA (vii) IMMEDIATE SOURCE:
            (B) CLONE: TRANSLATION OF pBEAR13

(xi) SEQUENCE DESCRIPTION: SEQ ID NO:43:

Glu Ser Thr Phe Phe Leu Arg His Leu Pro Val Ser Asn Ile Ser Glu
1               5                   10                  15

Ile Pro Asp Leu Asp Asp Gln Tyr Arg
            20                  25

(2) INFORMATION FOR SEQ ID NO:44:

(i) SEQUENCE CHARACTERISTICS:
            (A) LENGTH: 25 amino acids
            (B) TYPE: amino acid
            (C) STRANDEDNESS: single
            (D) TOPOLOGY: unknown (ii) MOLECULE TYPE: peptide (vi) ORIGINAL SOURCE:
            (A) ORGANISM: LYCOPERSICON ESCULENTUM (vii) IMMEDIATE SOURCE:
            (B) CLONE: ACO1

(xi) SEQUENCE DESCRIPTION: SEQ ID NO:44:

Glu Ser Thr Phe Phe Leu Arg His Leu Pro Thr Ser Asn Ile Ser Gln
1               5                   10                  15

Val Pro Asp Leu Asp Glu Glu Tyr Arg
            20                  25

(2) INFORMATION FOR SEQ ID NO:45:

(i) SEQUENCE CHARACTERISTICS:

(A) LENGTH: 25 amino acids
        (B) TYPE: amino acid
        (C) STRANDEDNESS: single
        (D) TOPOLOGY: unknown (ii) MOLECULE TYPE: peptide (vi) ORIGINAL SOURCE:
        (A) ORGANISM: LYCOPERSICON ESCULENTUM (vii) IMMEDIATE SOURCE:
        (B) CLONE: ACO2

(xi) SEQUENCE DESCRIPTION: SEQ ID NO:45:

Glu Ser Thr Phe Phe Leu Arg His Leu Pro Ser Ser Asn Ile Ser Gln
1               5                   10                  15

Leu Pro Asp Leu Asp Asp Val Tyr Arg
            20                  25

(2) INFORMATION FOR SEQ ID NO:46:

(i) SEQUENCE CHARACTERISTICS:
        (A) LENGTH: 25 amino acids
        (B) TYPE: amino acid
        (C) STRANDEDNESS: single
        (D) TOPOLOGY: unknown (ii) MOLECULE TYPE: peptide (vi) ORIGINAL SOURCE:
        (A) ORGANISM: LYCOPERSICON ESCULENTUM (vii) IMMEDIATE SOURCE:
        (B) CLONE: ACO3

(xi) SEQUENCE DESCRIPTION: SEQ ID NO:46:

Glu Ser Thr Phe Phe Leu Arg His Leu Pro Thr Ser Asn Ile Ser Gln
1               5                   10                  15

Val Pro Asp Leu Asp Glu Glu Tyr Arg
            20                  25

(2) INFORMATION FOR SEQ ID NO:47:

(i) SEQUENCE CHARACTERISTICS:
        (A) LENGTH: 55 amino acids
        (B) TYPE: amino acid
        (C) STRANDEDNESS: single
        (D) TOPOLOGY: unknown (ii) MOLECULE TYPE: peptide (vi) ORIGINAL SOURCE:
        (A) ORGANISM: BANANA (vii) IMMEDIATE SOURCE:
        (B) CLONE: TRANSLATION OF pBEAR13 after intron (xi) SEQUENCE DESCRIPTION: SEQ ID NO:47:

Lys Ala Met Lys Glu Phe Ala Ala Ala Ile Glu Lys Leu Ala Glu Arg
1               5                   10                  15

Leu Leu Asp Leu Leu Gly Glu Asn Leu Glu Leu Lys Gly Leu Leu
            20                  25                  30

Lys Lys Ala Phe Ser Asn Gly Ser Lys Gly Pro Thr Phe Gly Thr Lys
            35                  40                  45

Val Ser Asn Tyr Pro Pro Cys
        50              55

(2) INFORMATION FOR SEQ ID NO:48:

(i) SEQUENCE CHARACTERISTICS:
            (A) LENGTH: 54 amino acids
            (B) TYPE: amino acid
            (C) STRANDEDNESS: single
            (D) TOPOLOGY: unknown (ii) MOLECULE TYPE: peptide (vi) ORIGINAL SOURCE:
            (A) ORGANISM: LYCOPERSICON ESCULENTUM (vii) IMMEDIATE SOURCE:
            (B) CLONE: ACO1 AFTER INTRON (xi) SEQUENCE DESCRIPTION: SEQ ID NO:48:

Glu Val Met Arg Asp Phe Ala Lys Arg Leu Glu Lys Leu Ala Glu Glu
1               5                  10                  15

Leu Leu Asp Leu Leu Cys Glu Asn Leu Gly Leu Glu Lys Gly Tyr Leu
                20                  25                  30

Lys Asn Ala Phe Tyr Gly Ser Lys Gly Pro Asn Phe Gly Thr Lys Val
            35                  40                  45

Ser Asn Tyr Pro Pro Cys
    50

(2) INFORMATION FOR SEQ ID NO:49:

(i) SEQUENCE CHARACTERISTICS:
            (A) LENGTH: 53 amino acids
            (B) TYPE: amino acid
            (C) STRANDEDNESS: single
            (D) TOPOLOGY: unknown (ii) MOLECULE TYPE: peptide (vi) ORIGINAL SOURCE:
            (A) ORGANISM: LYCOPERSICON ESCULENTUM (vii) IMMEDIATE SOURCE:
            (B) CLONE: ACO2 AFTER INTRON (xi) SEQUENCE DESCRIPTION: SEQ ID NO:49:

Val Met Arg Asp Phe Arg Lys Arg Leu Glu Lys Leu Ala Glu Glu Leu
1               5                  10                  15

Leu Asp Leu Leu Cys Glu Asn Leu Gly Leu Glu Lys Ser Tyr Leu Lys
                20                  25                  30

Asn Thr Phe Tyr Gly Ser Lys Gly Pro Asn Phe Gly Thr Lys Val Ser
            35                  40                  45

Asn Tyr Pro Pro Cys
    50

(2) INFORMATION FOR SEQ ID NO:50:

(i) SEQUENCE CHARACTERISTICS:
            (A) LENGTH: 54 amino acids
            (B) TYPE: amino acid
            (C) STRANDEDNESS: single
            (D) TOPOLOGY: unknown (ii) MOLECULE TYPE: peptide (vi) ORIGINAL SOURCE:
            (A) ORGANISM: LYCOPERSICON ESCULENTUM (vii) IMMEDIATE SOURCE:
            (B) CLONE: ACO3 AFTER INTRON (xi) SEQUENCE DESCRIPTION: SEQ ID NO:50:

-continued

```
Glu Val Met Arg Asp Phe Ala Lys Arg Leu Glu Lys Leu Ala Glu Glu
1               5                   10                  15

Leu Leu Asp Leu Leu Cys Glu Asn Leu Gly Leu Glu Lys Gly Tyr Leu
            20                  25                  30

Lys Asn Ala Phe Tyr Gly Ser Lys Gly Pro Asn Phe Gly Thr Lys Val
        35                  40                  45

Ser Asn Tyr Pro Pro Cys
    50
```

RIPENING-RELATED DNAS FROM BANANA

This is a continuation of co-pending application Ser. No. 08/632,598 filed on Apr. 15, 1996 now U.S. Pat. No. 05,886,164.

BACKGROUND OF THE INVENTION

This application relates to DNAs, isolated from banana (*Musa*), DNA constructs containing the banana DNA, plant cells containing the constructs and plants derived therefrom. In particular it involves the use of antisense or sense RNA technology to control gene expression in plants.

Many physiological and developmental processes are controlled by ethylene in higher plants, including banana (Genus: *Musa*). These processes include fruit ripening where ethylene may be involved in both the initiation and rate of continuation of many of the changes involved in fruit ripening. However the exact role of ethylene has hitherto not been fully understood. We have now isolated a DNA involved in the generation of ethylene in bananas. In this invention, we provide such DNA, and methods of using it. One such use is a method for controlling the rate of production of ethylene in ripening bananas. In this way the rate of many of the ethylene-related changes associated with fruit ripening on a plant can be modified to obtain desired ripening characteristics.

The modification of plant gene expression has been achieved by several methods. The molecular biologist can choose from a range of known methods to decrease or increase gene expression or to alter the spatial or temporal expression of a particular gene. For example, the expression of either specific antisense RNA or partial (truncated) sense RNA has been utilised to reduce the expression of various target genes in plants (as reviewed by Bird and Ray, 1991, Biotechnology and Genetic Engineering Reviews 9:207–227). These techniques involve the incorporation into the genome of the plant of a synthetic gene designed to express either antisense or sense RNA. They have been successfully used to down-regulate the expression of a range of individual genes involved in the development and ripening of tomato fruit (Gray et al, 1992, Plant Molecular Biology, 19:69–87). Methods to increase the expression of a target gene have also been developed. For example, additional genes designed to express RNA containing the complete coding region of the target gene may be incorporated into the genome of the plant to "over-express" the gene product. Various other methods to modify gene expression are known; for example, the use of alternative regulatory sequences.

An object of the present invention is to provide new materials for use in the genetic control of ethylene biosynthesis in fruit, and hence ethylene-induced processes involved in fruit ripening, particularly banana fruit.

BRIEF SUMMARY OF THE INVENTION

According to a first aspect of the present invention, there is provided a method of modifying ethylene biosynthesis in a plant comprising inserting into the genome of the said plant a DNA sequence which modifies the activity of at least one of ACS or EFE.

Preferably, the said ACS has the sequence SEQ-ID-NO-1 and the said EFE has the sequence SEQ-ID-NO-2.

In particular, the method may be used to modify fruit ripening characteristics, especially in bananas.

The levels of ethylene biosynthesis may be either reduced or increased during development and ripening depending on the ripening characteristics desired for the modified fruit. "Antisense" or "partial sense" or other techniques may be used to reduce the expression of either ACS or EFE in developing and ripening fruit. The levels of ACS or EFE may also be increased; for example, by incorporation of additional ACS or EFE genes. The additional genes may be designed to give either the same or different spatial and temporal patterns of expression in the fruit.

The present invention provides clones of genes which express enzymes involved in ethylene biosynthesis: 1-aminocyclopropane-1-carboxylic acid synthase (ACS) and ethylene-forming enzyme (EFE). ACS and EFE are involved in ethylene production, and hence in the ripening of bananas. cDNA clones representing these genes have been cloned and characterised.

According to the present invention we provide cDNA clones representing at least part of genes derived from banana that encode either ACS or EFE. Example of such clones are clone pACS6 (ACS) and clone pACOS7 (EFE). We further provide DNA constructs comprising a DNA sequence homologous to some or all of genes derived from banana that encode either ACS or EFE, preceded by a transcriptional initiation region operative in plants, so that the construct can generate RNA in plant cells.

DETAILED DESCRIPTION OF THE INVENTION cDNA clones encoding a ACS and EFE have been obtained from a banana fruit pulp cDNA library. The clones are hereinafter called pACS6 (ACS) and pACOS7 (EFE). The full nucleotide sequence of the ACS cDNA (clone pACS6) is given as SEQ ID NO 1 and that of the EFE cDNA (clone pACOS7) is given as SEQ ID NO 2.

An alternative source of the DNA sequence is a suitable gene encoding either ACS or EFE. This gene may differ from the corresponding cDNA in that introns may be present. The introns are not transcribed into mRNA (or, if so transcribed, are subsequently cut out). Oligonucleotide probes or the cDNA clone may be used to isolate the actual ACS or EFE gene(s) by screening banana genomic DNA libraries. Such genomic clones may include control sequences operating in the plant genome. Thus it is also possible to isolate promoter sequences which may be used to drive expression of the enzymes or any other protein. These promoters may be particularly responsive to certain developmental events (such as ripening) and environment conditions. Banana ACS or EFE gene promoters may be used to drive expression of any target gene.

ACS or EFE DNA sequence may be isolated from banana cDNA or genomic DNA libraries using oligonucleotide probes based on the pACS6 or pACOS7 sequences. A banana ACS DNA sequence is any sequence from banana which cross-hybridises with SEQ ID NO 1, preferably having at least 60% homology with SEQ ID NO 1. A banana ACS DNA sequence may encode a protein which is homologous to the predicted gene product encoded by SEQ ID NO 1. A banana EFE DNA sequence is any sequence from banana which cross-hybridises with SEQ ID NO 2, preferably having at least 60% homology with SEQ ID NO 2. A banana EFE DNA sequence may encode a protein which is homologous to the predicted gene product encoded by SEQ ID NO 2.

A further way of obtaining ACS and EFE DNA sequence is to synthesise it ab initio from the appropriate bases, for example using the appropriate cDNA sequence as a guide.

Some or all of the ACS or EFE sequences may be incorporated into DNA constructs suitable for plant transformation. These DNA constructs may then be used to modify ACS or EFE gene expression in plants. "Antisense" or "partial sense" or other techniques may be used to reduce ACS or EFE gene expression in plant tissue (down-regulation). The levels of expression may also be increased (up-regulation); for example, by incorporation of additional ACS or EFE genes. The additional genes may be designed to give either the same or different spatial and temporal patterns of expression in the plant.

According to a further aspect of the invention there is provided a DNA construct comprising some or all of a ACS or EFE DNA sequence under the control of a transcriptional initiation region operative in plants, so that the construct can generate RNA in plant cells.

The fruit ripening characteristics and related characteristics of plant parts may be modified by transformation with a DNA construct according to the invention. The invention also provides plant cells containing such constructs; plants derived therefrom having modified ACS or EFE gene expression; and seeds of such plants.

A DNA construct according to the invention may be an "antisense" construct generating "antisense" RNA or a "sense" construct (encoding at least part of the functional enzyme) generating "sense" RNA. "Antisense RNA" is an RNA sequence which is complementary to a sequence of bases in the corresponding mRNA: complementary in the sense that each base (or the majority of bases) in the antisense sequence (read in the 3' to 5' sense) is capable of pairing with the corresponding base (G with C, A with U) in the MRNA sequence read in the 5' to 3' sense. Such antisense RNA may be produced in the cell by transformation with an appropriate DNA construct arranged to generate a transcript with at least part of its sequence complementary to at least part of the coding strand of the relevant gene (or of a DNA sequence showing substantial homology therewith). "Sense RNA" is an RNA sequence which is substantially homologous to at least part of the corresponding MRNA sequence. Such sense RNA may be produced in the cell by transformation with an appropriate DNA construct arranged in the normal orientation so as to generate a transcript with a sequence identical to at least part of the coding strand of the relevant gene (or of a DNA-sequence showing substantial homology therewith). Suitable sense constructs may be used to inhibit gene expression (as described in International Patent Publication W091/08299) or a sense construct encoding and expressing the functional enzyme may be transformed into the plant to over-express the enzyme.

DNA constructs according to the invention may comprise a base sequence at least 10 bases (preferably at least 35 bases) in length for transcription into RNA. There is no theoretical upper limit to the base sequence—it may be as long as the relevant mRNA produced by the cell—but for convenience it will generally be found suitable to use sequences between 100 and 1000 bases in length. The preparation of such constructs is described in more detail below.

As a source of the DNA base sequence for transcription, a suitable cDNA or genomic DNA or synthetic polynucleotide may be used. The isolation of suitable ACS or EFE sequences is described above. Sequences coding for the whole, or substantially the whole, of either enzyme may thus be obtained. Suitable lengths of these DNA sequences may be cut out for use by means of restriction enzymes. When using genomic DNA as the source of a partial base sequence for transcription it is possible to use either intron or exon regions or a combination of both.

To obtain constructs suitable for modifying expression of ACS or EFE in plant cells, the cDNA sequence as found in the enzyme cDNA or the gene sequence as found in the chromosome of the plant may be used. Recombinant DNA constructs may be made using standard techniques. For example, the DNA sequence for transcription may be obtained by treating a vector containing said sequence with restriction enzymes to cut out the appropriate segment. The DNA sequence for transcription may also be generated by annealing and ligating synthetic oligonucleotides or by using synthetic oligonucleotides in a polymerase chain reaction (PCR) to give suitable restriction sites at each end. The DNA sequence is then cloned into a vector containing upstream promoter and downstream terminator sequences. If antisense DNA is required, the cloning is carried out so that the cut DNA sequence is inverted with respect to its orientation in the strand from which it was cut.

In a construct expressing antisense RNA, the strand that was formerly the template strand becomes the coding strand, and vice versa. The construct will thus encode RNA in a base sequence which is complementary to part or all of the sequence of the enzyme mRNA. Thus the two RNA strands are complementary not only in their base sequence but also in their orientations (5' to 3').

In a construct expressing sense RNA, the template and coding strands retain the assignments and orientations of the original plant gene. Constructs expressing sense RNA encode RNA with a base sequence which is homologous to part or all of the sequence of the MRNA. In constructs which express the functional enzyme, the whole of the coding region of the gene is linked to transcriptional control sequences capable of expression in plants.

For example, constructs according to the present invention may be made as follows. A suitable vector containing the desired base sequence for transcription (such as the pACS6 or pACOS7 cDNA clones) is treated with restriction enzymes to cut the sequence out. The DNA strand so obtained is cloned (if desired, in reverse orientation) into a second vector containing the desired promoter sequence and the desired terminator sequence. Suitable promoters include the 35S cauliflower mosaic virus promoter or developmentally regulated fruit promoters. Suitable terminator sequences include that of the *Agrobacterium tumefaciens* nopaline synthase gene (the nos 3' end).

In a DNA construct according to the invention, the transcriptional initiation region may be derived from any plant-operative promoter. The transcriptional initiation region may be positioned for transcription of a DNA sequence encoding RNA which is complementary to a substantial run of bases in a mRNA encoding the ACS or EFE enzyme (making the DNA construct a full or partial antisense construct).

The transcriptional initiation region (or promoter) operative in plants may be a constitutive promoter (such as the 35S cauliflower mosaic virus promoter) or an inducible or developmentally regulated promoter (such as fruit-specific promoters), as circumstances require. For example, it may be desirable to modify ACS or EFE activity only during fruit development and/or ripening. Use of a constitutive promoter will tend to affect enzyme levels and functions in all parts of the plant, while use of a tissue specific promoter allows more selective control of gene expression and affected functions (eg fruit coloration). Thus in applying the invention it may be found convenient to use a promoter that will give expression during fruit development and/or ripening. Thus the antisense or sense RNA is only produced in the organ in which its action is required.

The DNA constructs of the invention may be inserted into banana plants to regulate the expression of ACS or EFE genes and the production of ACS or EFE enzymes, resulting in modification of plant characteristics (in particular fruit-ripening). Depending on the nature of the construct, the production of the ACS or EFE may be increased, or reduced, either throughout or at particular stages in the life of the plant. Generally, as would be expected, production of the enzyme is enhanced only by constructs which express RNA homologous to the substantially complete endogenous enzyme mRNAs. Full-length sense constructs may also inhibit enzyme expression. Constructs containing an incomplete DNA sequence shorter than that corresponding to the complete gene generally inhibit the expression of the gene and production of the enzymes, whether they are arranged to express sense or antisense RNA. Full-length antisense constructs also inhibit gene expression.

A DNA construct of the invention is transformed into a target banana cell. The target banana cell may be part of a whole plant or may be an isolated cell or part of a tissue which may be regenerated into a whole plant Plants may be derived from the transformed plant cell by regeneration of transformants and by production of successive clonal generations of the transformant.

Retardation of the rate of ripening will reduce the rate of deterioration of banana fruit after harvest. As a result of this fruit may be harvested when they have reached partial or full ripeness and still have the robustness to withstand handling and transport to reach the consumer in good condition. In this way high quality ripe fruit can be made available to the consumer with reduced requirement for post-harvest treatment. High quality fruit will have improved flavour and texture.

In addition high quality fruit can be produced consistently over a wide harvest period. Such fruit can be held in store for long periods and ripened to optimal quality by the supply of exogenous ethylene.

The invention will now be described further with reference to the accompanying drawings, in which:

EXAMPLE 1

Isolation of Banana ACS cDNA clones

The nucleic acid sequences from cloned ACS genes from 6 plant species were compared inorder to identify regions of maximum sequence conservation. Degenerate oligonucleotides based on these conserved regions were designed for use as PCR primers for amplification of ACS gene fragments from banana:

```
5' PRIMER:
Tomato        F   Q   D   Y   H   G   L            (SEQ-ID-NO-3)

Tomato        TTT CAA GAT TAT CAT GGC TTG          (SEQ-ID-NO-4)

Squash        TTT CAA GAT TAC CAT GGC TTA          (SEQ-ID-NO-5)

Mung Bean     TTT CAG GAT TAT CAT GGT CTG          (SEQ-ID-NO-6)

Tobacco       TTT CAA GAT TAT CAC GGC CTA          (SEQ-ID-NO-7)

Carnation     TTT CAG GAT TAT CAT GGT TTG          (SEQ-ID-NO-8)

Moth Orchid   TTT CAG GAC TAT CAT GGC CTC          (SEQ-ID-NO-9)

BACCS-2       5'-TTT CAR GAY TAY CAY GGY YTG-3'    (SEQ-ID-NO-10)
              (R = A or G; Y = T or C)
3' PRIMER:
Tomato        P   S   N   P   L   G   T            (SEQ-ID-NO-11)

Tomato        CCA TCA AAT CCA TTG GGC ACC          (SEQ-ID-NO-12)

Squash        CCC TCA AAT CCC TTA GGC ACA          (SEQ-ID-NO-13)

Mung Bean     CCA TCA AAT CCA TTA GGC ACA          (SEQ-ID-NO-14)

Tobacco       CCA TCA AAT CCA TTA GGC ACC          (SEQ-ID-NO-15)

Moth Orchid   CCT TCG AAT CCT CTG GGC ACC          (SEQ-ID-NO-16)

BACCS-4       5'-BGT KCC YAR DGG ATT TSA BGG-3'    (SEQ-ID-NO-17)
              (B = C or T or G; K = G or T; Y = C or T;
              D = T or G or A; S = G or C)
```

An 800 bp fragment was amplified from banana genomic DNA isolated from leaf tissue by PCR using these degenerate primers (Denaturation, 94° C. for 1 min; Annealing, 62° C. for 0.5 min; Extension, 73° C. for 2 min; 35 cycles; End extension 73° C. for 6 min). This PCR product was cloned into a plasmid vector to give the clone pBASH14 which was partially sequenced. 210 bp of sequence was determined at the 5' end of the clone. The encoded amino acid sequence showed significant homology (approx 90° C.) to tomato ACS genes LEACC1 and LEACC2 surrounding a 134 bp intron:

pBASH14=SEQ-ID-NO-18
TOMACC1=SEQ-ID-NO-20
TOMACC2=SEQ-ID-NO-21

```
pBASH14             TTTCAGGACTACCATGGTCTGCCGGACTTCCGTAAGTAATCACCGTCTGC

ID-NO-19            F  Q  D  Y  H  G  L  P  D  F  R  K <--------------

TOMACC1             F  Q  D  Y  H  G  L  P  E  F  R  K

TOMACC2             F  Q  D  Y  H  G  L  P  E  F  T  N

*  *  *  *  *  *  *  *     *

ATCCATAATGCAGCTCCTCGATCCTTACGCATGCGTGCCATGAACGATGA

------------------Intron-------------------------

GGGCACAGTTGGATCGATATGCGTTGCTATAGCCGAAAGTAATGACGCGA

-------------------------------------------------

TCATCTATGGAAATGCACAGGCCATTGCCAAGTTCATGGAGAAAGCGAGA

ID-NO-22            ------------------> A  I  A  K  F  M  E  K  A  R

TOMACC1 (SEQ-ID-NO-23)                   A  I  A  K  F  M  E  K  T  R

TOMACC2 (SEQ-ID-NO-24)                   A  I  A  K  F  M  E  K  T  R

*  *  *  *  *  *  *  *     *

GGAGGACGAGC

ID-NO-22            G  G  R

TOMACC1             G  G  R

TOMACC2             G  G  K

*  *
``` pBASH14 was used as a hybridisation probe to screen 400,000 clones of a cDNA library prepared from RNA extracted from ripening bananas. Eight hybridising plaques were identified and purified. Nucleotide sequence analysis showed that clone ACS6 encoded the complete ACS amino acid sequence when compared to ACS genes from other species.

Example 2

Isolation of Banana EFE cDNA Clones

The nucleic acid sequences from cloned EFE genes from 7 plant species were compared inorder to identify regions of maximum sequence conservation. Degenerate oligonucleotides based on these conserved regions were designed for use as PCR primers for amplification of EFE gene fragments from banana:

```
5' PRIMER:
Tomato      D    W    E    S    T    F    F              (SEQ-ID-NO-25)

Tomato      GAT  TGG  GAA  AGC  ACT  TTC  TTC            (SEQ-ID-NO-26)

Melon       GAC  TGG  GAA  AGC  ACT  TTT  TTT            (SEQ-ID-NO-27)

Peach       GAC  TGG  GAA  AGC  ACC  TTC  TAC            (SEQ-ID-NO-28)

Avocado     GAC  TGG  GAG  AGC  ACC  TTC  TTC            (SEQ-ID-NO-29)

Mustard     GAT  TGG  GAA  AGC  ACT  TTC  TAC            (SEQ-ID-NO-30)

Apple       GAC  TGG  GAA  AGC  ACC  TTC  TTC            (SEQ-ID-NO-31)

Carnation   GAT  TGG  GAG  AGC  ACC  TTC  TAC            (SEQ-ID-NO-32)

BEFE-5      5'-GAY TGG GAR AGC ACY TTY T -3'             (SEQ-ID-NO-33)
            (Y = T or C; R = A or G)
3' PRIMER
Tomato      V    S    N    Y    P    P    C              (SEQ-ID-NO-34)

Tomato      GTT  AGC  AAC  TAT  CCA  CCA  TGT            (SEQ-ID-NO-35)

Peach       GTT  AGC  AAC  TAC  CCT  CCT  TGT            (SEQ-ID-NO-36)
```

-continued

| | | |
|---|---|---|
| Apple | GTC AGC AAC TAC CCT CCA TGC | (SEQ-ID-NO-37) |
| Avocado | GTC AGC AAC TAC CCA CCC TGC | (SEQ-ID-NO-38) |
| Melon | GTT AGC AAT TAC CCC CCA TGT | (SEQ-ID-NO-39) |
| Mustard | GTG AGC AAC TAT CCA GCT TGT | (SEQ-ID-NO-40) |
| BEFE-2 | 5'-RCA DGG WGG RTA RTT GCT VAC-3'<br>(R = A or G; D = T or A or G; W = A or T;<br>V = A or C or G) | (SEQ-ID-NO-41) |

A 330 bp fragment was amplified from banana genomic DNA isolated from leaf tissue by PCR using these degenerate primers (Denaturation, 94° C. for 1 min; Annealing, 59° C. for 0.5 min; Extension, 73° C. for 2 min; 35 cycles; End extension 73° C. for 6 min). This PCR product was cloned into a plasmid vector to give the clone pBEAR13 which was fully sequenced. 210 bp of sequence was determined at the 5' end of the clone. The encoded amino acid sequence showed significant homology (approx 70–80%) to EFE genes from other species surrounding a 89 bp intron:

pBEAR13=SEQ-ID-NO-42

Aco1=SEQ-ID-NO-44

Aco2=SEQ-ID-NO-45

Aco3=SEQ-ID-NO-46

```
pBEAR13      GGGAGAGCACCTTTTTCCTGCGTCATCTCCCCGTCTCCAACATTTCTGAG
ID-NO-43      E  S  T  F  F  L  R  H  L  P  V  S  N  I  S  E
Tomato Aco1   E  S  T  F  F  L  R  H  L  P  T  S  N  I  S  Q
Tomato Aco2   E  S  T  F  F  L  R  H  L  P  S  S  N  I  S  Q
Tomato Aco3   E  S  T  F  F  L  R  H  L  P  T  S  N  I  S  Q
              *  *  *  *  *  *  *  *  *  *     *  *  *  * pBEAR13      ATCCCCGATCTTGATGACCAGTATAGGTTGCACGATCTGATCATGATGTC
              I  P  D  L  D  D  Q  Y  R<----------------------
              V  P  D  L  D  E  E  Y  R
              L  P  D  L  D  D  V  Y  R
              V  P  D  L  D  E  E  Y  R
                 *  *  *  *           * pBEAR13      ATCTTCTAGCCTTGTCTTTTCACCTTGCTCATCGTTTCGTTTCTTGGGAC
             --------------------Intron------------------------
pBEAR13      GATGACTGCGTGCAGGAAGGCGATGAAGGAATTTGCTGCAGCGATAGAGA
ID-NO-47     --------------->  K  A  M  K  E  F  A  A  A  I  E
ID-NO-48                        E  V  M  R  D  F  A  K  R  L  E
ID-NO-49                     -  V  M  R  D  F  R  K  R  L  E
ID-NO-50                        E  V  M  R  D  F  A  K  R  L  E
                                   *              *           * pBEAR13      AGCTGGCAGAGCGGCTGCTCGACTTGCTGGGTGAGAACCTGGAGCTGGAG
              K  L  A  E  R  L  L  D  L  L  G  E  N     L  E  L  E
              K  L  A  E  E  L  L  D  L  L  C  E  N     L  G  L  E
              K  L  A  E  E  L  L  D  L  L  C  E  N     L  G  L  E
              K  L  A  E  E  L  L  D  L  L  C  E  N     L  G  L  E
              *  *  *  *     *  *  *  *  *     *  *        *     * pBEAR13      AAGGGGCTCCTGAAGAAGGCCTTCTCTAATGGATCCAAGGGGCCAACCTT
```

```
                    -continued
         K  G  L  L  K  K  A  F  S  N  G  S  K  G  P  T  F

K  G  Y  L  K  N  A  F  -  Y  G  S  K  G  P  N  F

K  S  Y  L  K  N  T  F  -  Y  G  S  K  G  P  N  F

K  G  Y  L  K  N  A  F  -  Y  G  S  K  G  P  N  F

*        *  *           *        *  *  *  *  *        * pBEAR13  TGGGACCAAGGTCAGCAACTACCCACCTTGC

G  T  K  V  S  N  Y  P  P  C

G  T  K  V  S  N  Y  P  P  C

G  T  K  V  S  N  Y  P  P  C

G  T  K  V  S  N  Y  P  P  C

*  *     *  *  *  *  *  *  *
``` pBEAR13 was used as a hybridisation probe to screen 400,000 clones of a cDNA library prepared from RNA extracted from ripening bananas. 1200 hybridising plaques were identified. Nucleotide sequence analysis showed that clone ACOS7 encoded the complete EFE amino acid sequence when compared to EFE genes from other species.

Example 3

Construction of ACS Partial-Sense Vectors With a Constitutive Promoter.

A vector is constructed using sequences corresponding to a fragment of the insert of a banana ACS cDNA (isolated as shown in example 1). This fragment is synthesised by polymerase chain reaction using synthetic primers. The ends of the fragment are made flush with T4 polymerase and it is cloned into the vector pJR1 (Smith et al, 1988, Nature, 334:724–726) which has previously been cut with SmaI. pJR1 is a Bin19 (Bevan 1984, Nucleic Acids Research, 12:8711–8721) based vector which permits the expression of the ACO partial-sense RNA under the control of the CaMV 35S promoter. This vector includes a nopaline synthase (nos) 3' end termination sequence.

Example 4

Construction of EFE Partial-Sense Constructs With a Constitutive Promoter.

A vector is constructed using sequences corresponding to a fragment of the insert of a banana ACO cDNA (isolated as shown in example 2). This fragment is synthesised by polymerase chain reaction using synthetic primers. The ends of the fragment are made flush with T4 polymerase and it is cloned into the vector pJR1 (Smith et al, 1988, Nature, 334:724–726) which has previously been cut with SmaI. pJR1 is a Bin19 (Bevan 1984, Nucleic Acids Research, 12:8711–8721) based vector which permits the expression of the ACO partial-sense RNA under the control of the CaMV 35S promoter. This vector includes a nopaline synthase (nos) 3' end termination sequence.

Example 5

Generation of Transformed Banana Plants

Vectors are transferred to *Agrobacterium tumefaciens* LBA4404 (a micro-organism widely available to plant biotechnologists) and are used to transform banana plants. Transformation of banana meristems follow the protocols described by May et al (1995, Biotechnology 13:486–492). Transformed plants are identified by their ability to grow on media containing the antibiotic kanamycin. Plants are regenerated and grown to maturity. Ripening fruit are analysed for modifications to their fruit ripening characteristics.

What is claimed is:

1. A method of modifying the level of ethylene biosynthesis in a plant of the genus *Musa* comprising inserting into the genome of said plant a DNA sequence encoding a banana ACS or EFE, wherein said DNA sequence is in sense or antisense configuration, and wherein said DNA sequence modifies the level of activity of at least one of ACS or EFE.

2. The method as claimed in claim 1 wherein said DNA sequence has the sequence of SEQ ID NO: 1 or SEQ ID NO: 2.

3. A transgenic banana plant wherein the fruit of said plant has a retarded ripening phenotype, said phenotype resulting from an introduced transgene which inhibits ethylene synthesis, wherein said introduced transgene comprises a DNA sequence encoding a banana ACS or EFE which DNA sequence is in sense or antisense configuration and modifies the level of activity of at least one of ACS or EFE.

4. The transgenic banana plant as claimed in claim 3, wherein said transgene comprises the sequence of SEQ ID NO: 1 or SEQ ID NO: 2.

5. A fruit of the transgenic banana plant of claim 3.

6. A fruit of the transgenic banana plant of claim 4.

* * * * *